(12) United States Patent
Di Maio

(10) Patent No.: US 11,723,939 B2
(45) Date of Patent: Aug. 15, 2023

(54) COMPOSITION FOR GASTRIC AND OESOPHAGEAL DISEASES

(71) Applicant: NEILOS S.R.L., Piano di Sorrento (IT)

(72) Inventor: Umberto Di Maio, Piano di Sorrento (IT)

(73) Assignee: NEILOS S.R.L., Piano di Sorrento (IT)

( * ) Notice: Subject to any disclaimer, the term of this patent is extended or adjusted under 35 U.S.C. 154(b) by 0 days.

(21) Appl. No.: 17/253,756

(22) PCT Filed: Jun. 17, 2019

(86) PCT No.: PCT/IB2019/055031
§ 371 (c)(1),
(2) Date: Dec. 18, 2020

(87) PCT Pub. No.: WO2019/243991
PCT Pub. Date: Dec. 26, 2019

(65) Prior Publication Data
US 2021/0268055 A1   Sep. 2, 2021

(30) Foreign Application Priority Data

Jun. 18, 2018 (IT) .................. 102018000006400

(51) Int. Cl.
*A61K 36/48* (2006.01)
*A61P 1/04* (2006.01)
*A61K 31/728* (2006.01)
*A61K 31/765* (2006.01)

(52) U.S. Cl.
CPC ............ *A61K 36/48* (2013.01); *A61K 31/728* (2013.01); *A61K 31/765* (2013.01); *A61P 1/04* (2018.01)

(58) Field of Classification Search
CPC .... A61K 36/48; A61K 31/728; A61K 31/765; A61P 1/04
See application file for complete search history.

(56) References Cited

FOREIGN PATENT DOCUMENTS

| EP | 3184115 A1 | 6/2017 |
|---|---|---|
| WO | WO 2006/088305 A1 | 8/2006 |
| WO | WO 2015/158771 A1 | 10/2015 |
| WO | WO 2017/055909 A1 | 4/2017 |

OTHER PUBLICATIONS

Savarino et al. (Annals of Gastroenterology (2017); 30, 1-17).*
International Search Report and Written Opinion for International Application No. PCT/IB2019/055031, European Patent Office, Netherlands, dated Dec. 8, 2020, 13 pages.

* cited by examiner

*Primary Examiner* — Shirley V Gembeh
(74) *Attorney, Agent, or Firm* — Sterne, Kessler, Goldstein & Fox P.L.L.C.

(57) ABSTRACT

The present invention relates to a composition for oral use comprising an extract of *Tamarindus indica*, hyaluronic acid and/or its salts and at least one block copolymer of ethylene oxide and propylene oxide for the treatment of gastric and oesophageal diseases, in particular gastroesophageal reflux.

9 Claims, No Drawings

COMPOSITION FOR GASTRIC AND OESOPHAGEAL DISEASES

FIELD OF THE INVENTION

The present invention relates to a composition for oral use comprising an extract of *Tamarindus indica*, hyaluronic acid and/or its salts and at least one block copolymer of ethylene oxide and propylene oxide for the treatment of gastric and oesophageal diseases, in particular gastroesophageal reflux. This invention is based on the synergistic action of the aforementioned active ingredients.

PRIOR ART

The term "gastroesophageal reflux" means "the involuntary and subconscious passage of some of the gastric content into the oesophagus, without involvement of the gastric and abdominal musculature". The oesophagus is a long channel measuring 25-30 cm in length and connects the mouth to the stomach, wherein it is possible to distinguish along its length between two sphincter structures: the first between the hypopharynx and the cervical oesophagus the (upper oesophageal sphincter, or (UES)), and the second, the lower oesophageal sphincter (LES), at the oesophageal-gastric junction. The latter is a high-pressure zone, which represents the primary anti-reflux structure, thanks to its positioning between the negative-pressure intrathoracic zone and the positive-pressure intraabdominal zone. Thus, under normal conditions, a rise in abdominal pressure acts on the LES, preventing it from returning ingested material to the oesophagus. Under physiological conditions, the LES is closed and opens for a period of approximately 3-10 seconds after swallowing.

Other anatomical structures, apart from the LES, which help to maintain the anti-reflux barrier are:

- angle of His, acute angle formed between the oesophagus and the gastric fundus;
- the phrenoesophageal ligament;
- the diaphragmatic collar, formed by portions of the diaphragm arranged like a scarf around the oesophagus, throttling it during the inspiratory phase.

Numerous factors are taken into consideration in the pathogenesis of gastroesophageal reflux disease GERD), for example:

1. Insufficient anti-reflux barrier of the lower oesophageal sphincter, the purpose of which is to mechanically prevent the gastric juices from passing backward into the oesophagus.
2. Delay in gastric emptying, due to anatomical anomalies or changes: (i) anatomical anomalies: pyloric stenosis (the end region of the stomach, which regulates the passage of the gastric content in the duodenum); (ii) functional changes: motor changes to the fundus (region responsible for the emptying of liquids)
3. Insufficient oesophagus clearing mechanism, the purpose of which is to minimise contact between oesophageal mucosa and gastric juices, implemented both via oesophageal peristalsis and via the neutralisation of acid residues thanks to saliva.
4. Gastric hyperacidity.
5. Aggressive nature of gastric content, which passes back into the oesophagus due to the action of hydrochloric acid.
6. Duodenal gastric reflux with passage in the stomach of pancreatic-biliary secretions, which, in the case of gastroesophageal reflux, can result in more serious lesions.

Other predisposing factors include smoking, improper dietary behaviour habits (large meals, foods rich in fats, caffeine, medication, pregnancy and obesity can exacerbate GERD. Hiatus hernia (passage of part of the stomach into the thorax through a hole in the diaphragm, referred to as oesophageal hiatus) is also often accompanied by GERD and can contribute to prolonged exposure to the gastroduodenal contents. Generally, the walls of the oesophageal hiatus are well adhered to the oesophagus, however it can happen that the structures anchoring the lower portion of the oesophagus lose tone, promoting the ascension of a small part of the stomach into the thorax.

Whatever the cause, the frequent and repeated contact of regurgitated gastric content with the oesophageal mucosa, has a detrimental effect thereon, which becomes worse, the longer the time of contact and the lower the pH of the reflux. The persistent phlogistic action on the oesophageal mucosa becomes responsible over time for the inflammatory response, which can develop into ulcerations, into stenoses, and into what is known as columnar metaplasia (or Barret's mucosa, single biggest risk factor for the development of oesophageal adenocarcinoma). The symptoms considered to be typical are represented by heartburn (described by the patient as a burning sensation which starts in the stomach or in the lower portion of the thorax and reaches as far as the neck) and regurgitation (sensation of liquid with bitter and acidic taste within the oral cavity), the specificity of these symptoms for GERD being equal to 89 and 95% respectively. Symptoms that occur frequently but are less specific include odynophagia, dysphagia, belching, epigastric pain, bloating, and digestive difficulty. Some of these symptoms characterise the diagnosis of functional dyspepsia, and it is known that ±1 between 10% and 17% of patients who require medical intervention for dyspepsia have GERD.

GERD is one of the pathological conditions most frequently encountered by gastroenterologists.

A study on the prevalence of the disease revealed that GERD has a prevalence of 10-20% in Western countries compared to just 5% in Asia; in particular, the highest number of cases are encountered in North America, followed by northern Europe and southern Europe.

Scientific studies have demonstrated how the symptoms of the disease have a strong impact on quality of life insofar as the persistent symptoms of reflux, even during treatment with proton pump inhibitors for example, are associated with reduced physical and mental well-being.

This being a chronic disease, conventional treatment is almost always given over a long period of time and, depending on severity, consists of lifestyle changes (eliminating chocolate, caffeine, alcohol, smoking cigarettes, losing weight, etc.), medication, and surgery. Classes of drugs currently used in GERD include: antacid drugs, H2 histamine receptor antagonists and proton pump inhibitors (PPIs), and prokinetic agents.

Antacids are over-the-counter drugs which offer rapid relief from the symptoms of the disease, but are not able to provide a curative effect for erosive esophagitis. These drugs contain carbonates and bicarbonates which reduce the acidity in the stomach, reacting with hydrochloric acid and releasing carbon dioxide.

H2 antagonist drugs such as ranitidine, famotidine, and cimetidine guarantee temporary relief from the symptoms, although they have a slower onset time as compared to antacids. Use for extended periods of time is not recommended, since patients could develop a tolerance within 1-2 weeks and in any case the effect of these drugs is not curative in nature.

PPI drugs (pantoprazole, lansoprazole, omeprazole, etc.) in fact represent the standard treatment in gastroesophageal reflux diseases, the number of prescriptions for such drugs having doubled in the last 10 years. Such prescriptions are often combined with those for anti-inflammatory drugs, which may or may not be steroid-based. The mechanism of action of PPIs includes blocking the proton pump at the parietal cells of the stomach; this ATPase hydrogen/potassium pump determines the release of hydrochloric acid in the lumen of the stomach. Compared to H2 antagonist drugs, these drugs have a quicker action and above all have a curative effect with regard to oesophageal lesions. The side effects primarily encountered in treatment with PPI are constituted by nausea, diarrhoea, headache, insomnia and anaphylactic reactions.

Prokinetic agents, such as cisapride or metoclopramide, activate the serotonin or dopamine receptors so as to increase oesophageal or gastric peristalsis. These drugs have a slow onset of action, short duration, and do not have a curative effect on the disease. In addition, they have various side effects, such as tremors, dyskinesia, fatigue, and an increase in cardiac-related adverse events, for which reason their use in the treatment of GERD is rather limited.

In addition to the conventional pharmacological remedies, alginates are also used for symptomatic treatment of GERD. Alginates, such as alginate sodium, are natural polysaccharides which, upon contact with the gastric environment, precipitate within a few minutes to form a low-density gel. The change in pH triggered by bicarbonates and carbonates, which are also almost always present in the commercially available formulations, releases carbon dioxide, which is entrapped within the alginate gel, causing it to float above the gastric content. The alginate gel forms in the portion of the stomach close to the gastroesophageal junction, exactly where the acid pocket develops. In this way, it blocks or significantly reduces the ascension of stomach acid in the oesophageal channel. The object of the present invention is to provide an alternative composition compared to those known in the prior art, which is useful in the treatment of gastric and oesophageal diseases, in particular in gastroesophageal reflux disease.

SUMMARY OF THE INVENTION

The present invention is based on the discovery and identification of a new combination of active ingredients which have demonstrate a synergistic and improved action of the various components of the combination forming the subject of the invention.

The present invention relates to compositions comprising or consisting of a mixture of hyaluronic acid, an extract of *Tamarindus indica* and a block copolymer of ethylene oxide and propylene oxide. The present invention also relates to such compositions for use in the treatment of gastric and oesophageal diseases, in particular in gastroesophageal reflux disease.

The present invention provides the following advantages in a single composition:

Hyaluronic acid provides an essential component of the extracellular matrix of essential importance in repair processes and has the ability to promote cellular turnover and to repair mucosa damage caused by gastric disease.

The extract of *Tamarindus indica*, thanks to its content of polysaccharides, is able to adhere to the mucosas with a hydrating and soothing effect;

The polymers belonging to the class of polaxamers alone or in combination are able to form a gel at temperatures close to those encountered in the body, promoting adhesion of the formulation to the oesophageal, gastric and intestinal mucosas, ensuring a prolonged period of contact of the other functional active ingredients. Further advantages and features of the present invention will become clear from the following detailed description.

DETAILED DESCRIPTION OF THE INVENTION

The present invention describes a composition comprising hyaluronic acid and/or its salts, an extract of *Tamarindus indica*, and at least one polaxamer as main active ingredients.

Hyaluronic acid is an important component of the synovial liquid and of the extracellular matrix. Chemically, it is a natural polymer formed from alternate residues of glucuronic acid and n-acetyl-d-glucosamine and belongs to the class of substances known as glycosaminoglycans (GAGs). Within this class of compounds it is the compound having the simplest structure and is the only one non-covalently bonded to a protein and non-sulfated core. Fibroblasts are the main cells that release hyaluronic acid in the extracellular matrix.

Hyaluronic acid is involved in important physiological processes: repair and regeneration of wounds, and morphogenesis and structural organisation of the matrix itself. The biological role of hyaluronic acid is closely linked to its hydrophilic and hydrodynamic properties, which allow it to retain water and thus play an important structural role in cells.

The molar mass can be up to 107 Da, and, thanks to its viscoelastic and rheological properties, it is an interesting component for use in various medical applications. Hyaluronic acid can be used in a high or low molecular weight. The term "hyaluronic acid of high molecular weight" describes a hyaluronic acid having a molecular weight between 1.0 million Daltons and approximately 4.0 MDa. For example, the elevated molecular weight of hyaluronic acid could have a molecular weight of approximately 2.0 MDa. In another example it can have a molecular weight of approximately 2.8 MDa. The term "hyaluronic acid of low molecular weight" describes a hyaluronic acid having a molecular weight below approximately 1.0 MDa. Hyaluronic acid of low molecular weight can have a molecular weight between approximately 200,000 Da (0.2 MDa) to less than approximately 1.0 MDa, for example between approximately 300,000 Da (0.3 MDa) and approximately 750,000 (0.75 MDa).

The topical application of hyaluronic acid for example makes it possible to treat ulcers of the oral mucosa with rapid remission of the symptoms thanks its known anti-inflammatory properties.

It is used in patients with osteoarthritis of the knee by way of intraarticular injection, however, due to its lubricating action, it is also used in ophthalmic preparations, primarily in the form of drops, for ocular administration for dry eye syndrome.

With regard to the present invention, hyaluronic acid is particularly interesting on account of its protective, hydrating and soothing action on the mucosas of the gastro-oesophageal tract. In addition, its local anti-inflammatory action allows rapid relief of the symptoms associated with heartburn caused by contact of the tissues with hydrochloric acid. The ability of the compound to act on the prostaglandins, the metalloproteins and other inflammation mediators is known in the literature, Hyaluronic acid and its salts are valid bioactive ingredients for the preparation of pharmaceutical, nutraceutical and dermocosmetic products, or medical devices for the treatment of gastroesophageal reflux thanks to the hydrating, protecting and regenerating action in the tissues of the gastrointestinal mucosa.

Tamarind (*Tamarindus indica*) is an evergreen tree which grows up to 24 metres in height and 7 metres in circumference with yellow and pink flowers. It requires a dry climate in order to grow, and in fact is very widespread in Africa from Senegal to Sudan, in Ethiopia, Mozambique, Madagascar, etc. All of the parts of the plant (roots, trunk, fruit, leaves) have great nutritional value. They can therefore be used in the form of extracts of the roots, trunk, fruit, seeds, leaves or mixtures thereof.

In the compositions of the present invention, extracts of tamarind in the form of dry or hydroalcoholic extracts can be used for example, as are commercially available or obtained by methods known to those skilled in the art. According to the World Health Organisation, the fruit of the plant is an ideal source of all essential amino acids, with the exception of tryptophan. The seeds are also of comparable nutritional value and represent an important source of protein in countries where there is widespread malnutrition. The uses of the plant are many: as a laxative (in particular the fruits, due to their high content of malic and tartaric acid), as smooth muscle relaxant (the fruit, due to its calcium channel blocker action) as an antimicrobial, antioxidant, anti-diabetic, anti-inflammatory, etc.

In particular, the seeds of tamarind are rich in polysaccharides, including the xyloglucan molecules formed by a linear skeleton of β-1-4 glucans with short lateral branchings which can contain other sugars, such as arabinose and fucose, thus changing the name respectively to arabino xyloglucans and fucogalacto xyloglucans. The seeds of tamarind, thanks to their high content of polysaccharides, can be used in skin creams and in drops or other ophthalmic preparations, thanks to their mucoadhesive ability. With regard to the present invention, the extracts of tamarind and in particular the fractions rich in polysaccharides can be used in the treatment of pathologies such as gastroesophageal reflux. In fact, after having been administered orally, the polysaccharides of tamarind, due to their pronounced mucoadhesive properties, can coat the walls of the gastrointestinal tract, protecting it against the action of the acid and providing a soothing and emollient effect.

The term "polaxamer" means a series of polymers of ethylene oxide and of propylene oxide. In particular, it refers to triblock copolymers with the following exemplary structural formula:

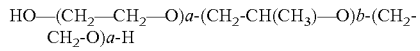

HO—(CH$_2$—CH$_2$—O)a-(CH$_2$-CH(CH$_3$)—O)b-(CH$_2$-CH$_2$-O)a-H

All of the compounds belonging to this class have similar molecular structures, also indicated by the acronym PEG-PPG-PEG, with differences in the molecular weight and in the composition of the polyoxyethylene blocks (a) and polyoxypropylene blocks (b).

Among these polymers, the most commonly used are poloxamer 188 (where a=80 and b=27), with a molecular weight between 7680-9510 Da and poloxamer 407 (a=101 and b=56) with molecular weight ranging from 9840 to 14600 Da. Such polymers enjoy wide use in pharmaceutical preparations, such as surfactants, emulsifiers, solubilisers, dispersants, and absorption enhancers. Commercial names of these products include Pluronic, Synperonic, Kolliphor.

Other polaxamers, selected from the group of poloxamer 101, poloxamer 105, poloxamer 105 benzoate, poloxamer 108, poloxamer 122, poloxamer 123, poloxamer 124, poloxamer 181, poloxamer 182, poloxamer 182 dibenzoate, poloxamer 183, poloxamer 184, poloxamer 185, poloxamer 188, poloxamer 212, poloxamer 215, poloxamer 217, poloxamer 231, poloxamer 234, poloxamer 235, poloxamer 237, poloxamer 238, poloxamer 282, poloxamer 284, poloxamer 288, poloxamer 331, poloxamer 333, poloxamer 334, poloxamer 335, poloxamer 338, poloxamer 401, poloxamer 402, poloxamer 403 and poloxamer 407 or mixtures thereof can also be used.

These are thus functional excipients insofar as they play a fundamental role in the formulations. Once of the most interesting properties of such polymers is their ability for sol-gel transition depending on temperature. It has been demonstrated that the composition of the polymer influences the solubility and temperature of sol-gel transition in aqueous solutions: the solubility in water of the polyoxyethylene block is increased in a temperature range of from 0 to 100° C., whereas the solubility of the polyoxypropylene block decreases at temperatures above 15° C. The mechanism of gelification is based on the solubility of the polyoxypropylene block. An increase in temperature above the temperature of micellization leads to an aggregation of the central portion (of polyoxypropylene) of the polymer, with subsequent formation of micelles having a polyoxypropylene core and polyoxyethylene side chains. A further rise in temperature leads to the gelification of the micelles. This results from the packing of the micellar structures.

Polaxamer 407 forms aqueous solutions that have a sol-gel transition temperature around 25° C., whereas solutions of polaxamer 188 have a sol-gel transition temperature greater than 40° C. By preparing aqueous solutions of mixtures of the two polymers, it is possible to have gelification at intermediate temperatures.

Polaxamers therefore have interesting mucoadhesive properties that are of particular importance from a technical viewpoint and that can be particularly advantageous for the present invention. Specifically, the use of a polaxamer or of a mixture thereof allows adhesion of the formulation to the mucosas of the oesophageal, gastric and intestinal tracts, preventing contact with the material produced as a result of the gastric reflux and causing damage to the mucosas. In addition, its mucoadhesive capability ensures prolonged contact of the formulation and therefore of the functional active ingredients so as to increase efficacy and reliability.

The inventors observed the best synergistic action among the various active ingredients at the following concentrations:
  the extract of *Tamarindus indica* in an amount by weight between 10 mg and 5000 mg;
  hyaluronic acid and/or its salts present in a concentration by weight between 1 mg and 2000 mg;
  poloxamer present in an amount by weight between 1 and 2000 mg.

The compositions according to the present invention can be formulated in any form and for any administration method and can be combined with any other component, in a variety of ways, but preferably are formulated for oral use and for example in the form of capsules, soft capsules, tablets, pills, gelatins, powders or granules, solutions, suspensions, gels, syrups, or elixirs. Such excipients can be selected for example from those known routinely in the art and include, although this list is not limiting: a) vehicles, for example sodium citrate and calcium phosphate; b) fillers, such as amide, lactose, microcrystalline cellulose, sucrose, glucose, mannitol and colloidal silica; c) humectants, such as glycerol; d) disintegrants, such as alginates, calcium carbonate, amides, derivatives of amide, of cellulose and of polyvinylpyrrolidone, silicates and sodium carbonate; e) binders, such as carboxymethylcellulose, alginates, gelatin, polyvinylpyrrolidone, sucrose, polymer derivatives of cellulose, derivatives of amide; f) retardants, such as paraffin, cellulose polymers, fatty acid esters; g) absorption accelerators, such as quaternary ammonium compounds; h) wetting agents and surfactants, such as cetyl alcohol and glycerol monostearate; i) adsorbents, such as bentonite and kaolin clays, k) lubricants, such as talc, calcium stearate, magnesium stearate, polyethylene glycol, sodium laureth sulphate, sodium stearyl fumarate; j) slip agents, such as talc, colloidal silica.

The solid dosage forms, such as tablets, capsules, soft capsules, gelatins, pills and granules, can be coated by coatings of the enteric or gastric type or of other types known in the prior art. They can contain opacifying agents and can be of such a type as to allow the active ingredients to be released only or preferably in a particular section of the intestine, possibly in a delayed manner. Substances that can allow such a delayed use include, but are not limited to, polymers and waxes.

Soft capsules can contain the antioxidant active ingredients in liquid form alone or in solutions, suspensions or emulsions of the active substances in a liquid solvent. Soft capsules can be characterised by a casing that is similar qualitatively to that of hard capsules, but is thicker and soft.

Liquid forms suitable for oral administration are, for example, emulsions, solutions, prepared or extemporary suspensions, syrups and elixirs. Excipients suitable for the formulations according to the present invention in liquid form for oral use include, but are not limited to, diluents, including water or other solvents, solubilising and emulsifying agents selected from ethyl alcopropylene glycol, glycerol, polyethylene glycol and sorbitol esters. These formulations can also contain sweeteners and flavourings.

The compositions will be for example a medical device, food supplement, a nutraceutical, dietary and nutritional composition, a foodstuff, a beverage, a nutraceutical, a medicament, a medicated food, a food for special medical purposes, or a food. The compositions will be intended primarily for use by human beings, but could also be used in animals.

The combination of the above-mentioned active ingredients can be used formulated in a single composition according to the various embodiments described above or in a kit containing the various ingredients separately, for example in single compositions such as capsules or pills for sequential or concomitant administration of the various ingredients.

The compositions and the kits described above can be used/administered/consumed for the treatment of gastric or oesophageal diseases, in particular for gastroesophageal reflux.

EXAMPLES

Some non-limiting examples of daily doses of the combination of active ingredients used in the compositions of the present invention are presented below.

| EXAMPLE 1 | |
|---|---|
| Active ingredient | Daily dose |
| Tamarindus indica e.s. | 100 mg |
| Hyaluronic acid | 10 mg |
| Poloxamer 407 | 20 mg |

| EXAMPLE 2 | |
|---|---|
| Active ingredient | Daily dose |
| Tamarindus indica e.s. | 200 mg |
| Hyaluronic acid | 50 mg |
| Poloxamer 407 | 10 mg |
| Poloxamer 188 | 10 mg |

| EXAMPLE 3 | |
|---|---|
| Active ingredient | Daily dose |
| Tamarindus indica e.s. | 50 mg |
| Hyaluronic acid | 10 mg |
| Poloxamer 407 | 50 mg |

| EXAMPLE 4 | |
|---|---|
| Active ingredient | Daily dose |
| Tamarindus indica e.s. | 150 mg |
| Hyaluronic acid | 100 mg |
| Poloxamer 407 | 25 mg |
| Poloxamer 188 | 25 mg |

Experimental Data

The authors of the present invention found that the simultaneous administration of the active ingredients selected by them provides a more effective treatment of gastroesophageal reflux in subjects in need, as compared to a therapy in which the active ingredients are administered separately.

The synergistic action of the individual components was assessed by means of invitro or in vivo methods.

Tests in vitro include for example the study of viscosity as a function of the temperature or other applicable parameters able to demonstrate any kind of improved effect attributed to the synergy of the three components.

The synergistic activity of the components can be assessed in vitro by means of mucoadhesion tests performed on cells (for example on epithelial cells of the buccal mucosa) or by means of other validated methods (for example inclined plane with mucin).

In vivo methods used to assess the anti-reflux effect of the formulation compared to single components are: gastric emptying, and/or reflux oesophagitis, and/or gastric secretion, and/or gastric ulcer. Such parameters are assessed after administration to animals of the single components and their combination.

Gastric emptying was performed on mice or rates to whom a suspension of phenol red in carboxymethylcellulose had been administered. After approximately 20 minutes the animals were killed in an atmosphere saturated with $CO_2$ and the stomach was removed and positioned in a tube of physiological solution. An amount of NaOH was added to each tube to develop the maximum intensity of colour. Then, analyses be spectrophotometry were performed (560 nm) and the percentage of gastric emptying was calculated by the following formula:

$$100 \times (1-[\text{amount of phenol red present in the stomach after 20 minutes}]/[\text{amount of phenol red present in the stomach at time 0}])$$

Reflux oesophagitis and gastric secretion were induced, with the animals having free access to water with fasting for 24 hours; the animals were then anaesthetised, the abdomen opened, and the pylorus was tied. After approximately 4 hours after the surgical procedure, the mice were killed in an atmosphere saturated with $CO_2$ and the stomach and oesophagus were removed for the purpose of assessing: macroscopic oesophageal and gastric damage, the degree of oesophageal and gastric inflammation (myeloperoxidase activity), volume of the gastric contents, pH and total acidity. Formalin was used as reference drug administered at a dose of 40 mg/Kg.

The invention claimed is:

1. A method of treating gastric or esophageal diseases comprising administering a therapeutically effective amount oft a composition for oral use comprising an extract of *Tamarindus indica*, hyaluronic acid and/or its salts and at least one block copolymer of ethylene oxide and propylene oxide to a subject in need thereof.

2. The method of claim 1, wherein said disease is gastroesophageal reflux.

3. The method according to claim 1, wherein said copolymer is a poloxamer.

4. The method according to claim 3 wherein the poloxamer is selected from the group of poloxamer 101, poloxamer 105, poloxamer 105 benzoate, poloxamer 108, poloxamer 122, poloxamer 123, poloxamer 124, poloxamer 181, poloxamer 182, poloxamer 182 dibenzoate, poloxamer 183, poloxamer 184, poloxamer 185, poloxamer 188, poloxamer 212, poloxamer 215, poloxamer 217, poloxamer 231, poloxamer 234, poloxamer 235, poloxamer 237, poloxamer 238, poloxamer 282, poloxamer 284, poloxamer 288, poloxamer 331, poloxamer 333, poloxamer 334, poloxamer 335, poloxamer 338, poloxamer 401, poloxamer 402, poloxamer 403 and poloxamer 407 or their mixture.

5. The method according to claim 1 wherein the polymer is poloxamer 188 and/or poloxamer 407.

6. The method according to claim 1, wherein the composition in a form selected from capsule, soft capsule, tablet, pill, gelatin, powder, granule, emulsion, solution, suspension, gel, or syrup.

7. The method according to claim 1, wherein
the *Tamarindus indica* extract is in a concentration by weight of from 10 mg to 5000 mg, and/or
hyaluronic acid and/or its salts are in a concentration by weight of from 1 mg to 2000 mg, and/or
the copolymer is in a concentration by weight between 1 and 2000 mg.

8. The method according to claim 1, wherein said composition is a medical device, a food supplement, a nutraceutical, dietary and nutritional composition, a foodstuff, a beverage, a nutraceutical, a medicament, a medicated food or a food for special medical purposes.

9. The method according to claim 1, wherein
the *Tamarindus indica* extract is in a concentration by weight of from 10 to 600 mg; and/or
the hyaluronic acid and/or its salts are in a concentration by weight of from 10 to 600 mg; and/or
the copolymer is in a concentration by weight between 10 and 500 mg.

* * * * *